United States Patent [19]

Stahlhut

[11] Patent Number: 5,279,953
[45] Date of Patent: Jan. 18, 1994

[54] IN VIVO PRODUCTION OF TAXANES

[75] Inventor: Roy W. Stahlhut, Belmont, Calif.

[73] Assignee: ESCA Genetics Corporation, San Carlos, Calif.

[21] Appl. No.: 904,371

[22] Filed: Jun. 24, 1992

[51] Int. Cl.$^5$ .................. C12N 15/00; C12P 17/02; C12P 7/22; C07D 305/00

[52] U.S. Cl. .................. 435/172.3; 435/123; 435/156; 549/510

[58] Field of Search .................. 435/156, 170, 123, 41, 435/240.4, 240.48; 549/510

[56] References Cited

U.S. PATENT DOCUMENTS 5,019,504  5/1991  Christen et al. .................. 435/123

FOREIGN PATENT DOCUMENTS 0224287  3/1987  European Pat. Off. ...... C12N 15/00

OTHER PUBLICATIONS

E. Weiler et al. Trends in Biochem. Sci., vol. 12 (1987) pp. 271–275.
Luckner et al, Planta Medica 56:498–499 (1990), Cardenolide Accumulation in Crown Galls and Cell Lines Obtained by Transformation of *Digitalis lanata* with *Agrobacterium tumefaciens* Wild-Type Strains.
Cosio, E., et al J. Plant Physiol 124:155–164, Production of Antibiotic Thiarubrines by a Crown gall Tumor Line of *Chaenactis douglasii*.
Estramareix, C., et al. Plasmid, vol. 15 (1986) pp. 245–247.
Hanold, Dagmar, In Vitro Transformation of Protoplast-Derived *Hyoscyamus Muticus* Cells by *Agrobacterium Tumefaciens*, Plant Science Letters, 30 (1983) 177–183.
Science News, Feb. 22, 1992, p. 124.
Zambryski, P., et al. Cell, vol. 56 (1989) pp. 193–201.
Gasser, C., and Fraley, R., Transgenic Crops, Scientific American, Jun. 1992, pp. 62–69.
Komari, T., Plant Science, vol. 60 (1989) pp. 223–229.
de Cleene, M., A Possibility for Increasing the Production of Physiologically Active Substances by In Vitro Plant Tumour Cultures, Speculations in Science and Technology, vol. 3, No. 3, Aug. 1988 (Elsevier).
Esau, K, Plant Anatomy, 2nd Edition, N.Y., John Wiley & Sons, 1965, pp. 404–405.
Norton, R., Finlayson, A., and Towers, G., Thiophene Production by Crown Galls and Callus Tissues of *Tagetes Patula*, Phytochemistry vol. 24, No. 4, pp. 719–722, 1985.
Koziel, Michael G. et al, A Cauliflower Mosaic Virus Promoter Directs Expression of Kanamycin Resistence in Morphogenic Transformed Plant Cells. Journal of Molecular & Applied Genetics, (1984) New York; 2: 549–562.
Huizing, H., et al Acta Botanica Neerlandica, 35(1):47 (1986).

*Primary Examiner*—David T. Fox
*Assistant Examiner*—Charles Rories
*Attorney, Agent, or Firm*—Jacques M. Dulin

[57] ABSTRACT

Method for improved in vivo production of taxanes by inoculation of tissue of the genus Taxus with virulent or avirulent strains of Agrobacterium. In the preferred embodiment, virulent Agrobacterium is the inoculant which induces gall formation at all stages of the plant, from saplings to mature trees. Incomplete harvesting of galls permits regeneration on the trees, resulting in a renewable resource. Unexpectedly, the inoculant tissue (both virulent and avirulent) produces approximately twice the concentration of taxanes per unit tissue weight as compared to normal tissue. In addition, the virulent strain induced gall biomass is 2–3 times greater than normal tissue per unit growth time, while avirulent inoculants show approximately the same growth as normal. The net yield increase is 2–6 times normal, (4–6 for galls), is renewable, does not require special growth hormones or media, does not result in sacrificing the tree, and can be started at the sapling stage. The post-growth phase production is uncoupled by the inoculation and concentration yield is doubled.

12 Claims, No Drawings

IN VIVO PRODUCTION OF TAXANES

FIELD

This invention relates to an in vivo process for production of complex taxane-type alkaloid compounds (including taxol), and more particularly to the induction of galls by various agents introduced into tissues of trees of the genus Taxus, preferably virulent or avirulent Agrobacterium, followed by harvesting of the gall tissue and extraction of the taxane-type compounds therefrom.

BACKGROUND

The group of complex terpene-type compounds known as taxanes have proven to have important anti-cancer properties. The reference herein to taxane, taxane-type compounds or taxol will be shorthand for this recognized group of compounds having anti-cancer activity and other properties.

The primary source of the anti-cancer drug taxol is bark tissue of *Taxus brevifolia*, the Western (Pacific) yew. The supply of this drug is limited by the number of these slow-growing trees available for harvest. Using current methods, trees are cut and bark is removed. The most bark is, of course, obtained from mature trees. Cutting, however, kills the tree and reharvesting awaits 20 years or more for regrowth. The rate of cutting threatens wild trees with extinction.

The yield of taxol/taxane compounds is measured in micrograms per pound of plant bark where the highest concentration of taxol is normally found. For example, to obtain 1 gram of taxol requires harvesting some 22 lbs. of bark which represents 2-3 mature trees of age 20-40 years. A typical cancer treatment involves from 1 to 2 grams per patient over the course of the treatment regime extending 3-6 months.

A variety of processes have been proposed for sources of taxol/taxanes and their derivatives, including: Callus cell culture techniques, managed tree farms, and classic organic synthesis.

For example, U.S. Pat. No. 5,019,504 of Christen et al. is directed to culturing selected tissue, preferably bark or cambial tissue, from *Taxus brevifolia*. Since cultured plant tissue ordinarily does not produce the same compounds in culture, culturing is not always successful and is tricky to maintain. That is, taxol production is non-growth associated, involving secondary metabolism. Culturing may interfere with the secondary metabolism products, although there is no uncoupling of the post-growth relationship as taxol/taxanes are not usually produced during the initial callus proliferation stage. Further, taxol production after suspension cell culture growth is best induced by fungal or inorganic elicitors in subcultures, the best results being shown in subcultures supported on special agar media.

In Science News, Feb. 22, 1992, page 124, it is reported that a variety of workers are attempting various organic syntheses, which are difficult. Growing vast numbers of trees on managed tree farms is another approach, but that takes time as taxol is produced in the older plants. It is climate limited, labor intensive, and requires an enormous investment in land and harvesting equipment.

Gasser and Fraley, in an article entitled Transgenic Crops, Scientific American, June 1992, p. 62 describes the formation of crown galls by the plant pathogen *Agrobacterium tumefaciens*. "This bacterium can transfer a portion of its DNA into plant cells. It does so by introducing a set of genes into one or more of its own [sic] DNA fragments. These fragments called transferred DNA (T-DNA), then integrate into chromosomes of infected plant cells and induce the cells to produce elevated levels of plant hormones. These hormones cause the plant to form novel structures, such as tumors or prolific root masses, that provide a suitable environment and nutrient source for the Agrobacterium strain. This bacterial infection is crown gall disease." The Sanford DNA particle gun used for plant genetic transformation is shown in this article.

Also, De Cleene, in a letter in Speculations in Science and Technology, Vol. 3, No. 3, August 1980, Elsevier Sequoia, Lausanne, pp. 353-356, proposed consideration of in vitro cell and tissue cultures of crown gall tissue as a source of physiologically active substances because of their possible greater metabolic activity. He cautioned that "It is true that the biosynthetic pathways are not necessarily the same for normal and crown gall tissues. Biochemical differences between both tissue types have been suggested in the literature, but crown gall tumors nevertheless seem to reflect the physiological state of the host plant from which it developed. So there is a good chance that therapeutically active compounds are synthersized in both healthy and crown gall tumors of a certain plant species." In inviting experimentation along this line of speculation, De Cleene listed some 22 species, one of which was "*Taxus brevifolia* Nutt. (Western yew): anti-tumor agent, cyanogenetic glycoside (taxiphyllen)."

Subsequent research dampened De Cleene's speculations. Thus, Norton et al. in Phytochemistry Vol. 24, No. 4 pp. 719-722 (1985) measured thiophene concentrations in crown gall tissue produced by *Agrobacterium tumefaciens* strains A208 and A277 of *Tagetes patula* plants (Marigold-French Dwarf Double, Sparky Mixed) and concluded that: "The results showed it is not possible to predict the amounts of secondary metabolites produced as a result of transfers of genetic material from infected plants to crown galls and then to transformed callus tissues." They also noted that: "Most of the publications to date (1985) contain results which show a reduced yield of secondary metabolite production by crown gall tissues or transformed callus tissues."

Huizing, H., Hibma, J. and Wichers, H., reported in Acta Botanica Neerlandica, 35(1):47 (1986) on their investigation of the feasibility of production of L-DOPA on crown-gall tumour tissue of *Nucuna puriens* (a dicot). Tumors were initiated on plants, removed and placed in culture to obtain hormone autotrophic cell lines. Transformed cells did not produce more L-DOPA than did cells which were grown in the presence of growth regulators.

Luckner, M., Moldenhauer, E., First, B., and Dietrich, B., in Plant Medica 56:498-499 (1990) reported on cardenolide accumulation in crown galls and cell lines obtained by transformation of *Digitalis lanata* (a dicot) with wild-type strains of *Agrobacterium tumefaciens*. Tumors were induced on sterile leaf disks obtained from greenhouse or in vitro plants and the tissue analyzed for digitoxin derivatives. The average content of products was only 30% that of the leaves the galls were attached to, but in some cases exceeded concentrations in the leaf. For digoxin, the results were different. Crown galls only contained about 1% that of the leaf.

Cosio, E., Norton, R., Towers, E., Finlayson, A., Rodriguez, E., and Towers, G. reported in J Plant Physiol 124:155-164 (1986) on production of antibiotic thiarubrines by a crown gall tumor line of *Chaenactis douglasii* (a dicot). They worked with a crown gall tumor line in vitro. They interpret their results as evidence of tissue organization in tumors being necessary for product formation. No data on freshly excised tumors was presented.

Accordingly, there is a need in the art to provide a process for increasing the rate of growth and concentrations in naturally growing Taxus tissue for increased yields of taxol/taxane-compounds.

THE INVENTION

Objects

It is among the objects of this invention to provide a method for improving the effective yield of taxol/taxane compound-containing biomass, and more particularly, biological tissues having the highest concentration of taxane compounds.

It is another object of this invention to provide a method for inducing rapidly growing gall tissue in established living plants, particularly the genus Taxus, which gall tissue has the capability of producing high concentrations of taxol/taxane-type compounds.

It is another object of this invention to transform the plant tissues, particularly of the genus Taxus, to induce them to produce galls which have the capability of producing taxane compounds in higher than normal yields during the growth phase.

It is another object to provide a method of inducing gall formation in Taxus plant tissue by inoculation with Agrobacterium, and to subsequently harvest the galls as a renewable resource and extract taxane-type compounds from the gall tissue produced.

It is another object of the invention to induce plant tissue response with virulent or avirulent Agrobacterium strains to produce inoculant tissue in Taxus trees of ages ranging from seedlings to mature trees, which inoculant tissues have growth rates ranging from normal to increased rates and which have higher than normal concentrations of taxanes.

Still other objects will be evident from the specification and claims of this application.

SUMMARY

The invention comprises a method for in vivo production and extraction of taxol/taxane-type compounds from inoculant tissue, and more particularly to the induction of plant tissue response in established living plants of the genus Taxus by use of virulent and avirulent Agrobacterium strains.

Galls are produced in the case of virulent inoculation. The galls are induced by a variety of simple techniques, including direct wounding of the plant tissue and introduction thereby of the selected Agrobacterium strain. The galls form rapidly, and can be harvested without harming the living tree. This process avoids a very unfortunate result of the current scientific interest in taxol from yew tree bark, which is that trees are killed upon being cut down in order to remove the bark. At the least, bark removal puts the tree under strain, subjecting the tree to potentially slowed growth or the tree becoming infested by insects or other natural enemies.

Surprisingly, it has been discovered that by inducing gall formation, the proliferation of cambium tissue by a suitable vector, the post-growth taxol production relationship is uncoupled. The inoculated tissue, whether induced by virulent or avirulent strains, has a higher concentration of taxol/taxane compounds resulting in a greater taxol/taxane yield per unit mass of tissue. Further, in the case of the virulent strain gall, there is an even greater yield due to the more rapid growth of the gall with a resultant greater total biomass produced per unit time as compared to the normal post-growth differentiated tissue in which it is induced. In avirulent inoculated tissue the yield is approximately twice normal (concentration increase only), and in virulent gall tissue it is approximately a four to six-fold yield increase (concentration and tissue mass increase) per unit growth time.

Equally important is that the galls can be harvested without substantial injury to the tree, and will then regrow, thus providing a renewable resource which neither kills nor stunts the tree. Once the gall has been induced and formed, it can be harvested so that successive galls can regrow and be reharvested without the need for reinoculation.

Further, the gall can be introduced into the tree at any age, including during the extremely young seedling or sapling stage. Taxol/taxane production by this invention does not require either substantial tree growth size or plant age (maturation) before any harvesting. The taxane-producing tissue becomes available much sooner under the process of this invention.

The extraction of the taxane compounds, including taxol, is straightforward. The gall tissue can be harvested, and then divided and extracted with standard solvents such as polar or semi-polar solvents such as methanol and ethanol, ether and methylene chloride. Surprisingly, the quantity of taxane compounds produced per gram of the inoculant tissue (both virulent gall and avirulent inoculated tissue) exceeds natural bark by a factor of approximately two, and it is bark which has the highest concentration of taxanes in natural tissue. In the usual cell culture situation, the cultured tissue must go through a growth phase before it will begin production of taxol compounds; i.e. the culturing does not uncouple the natural post-growth phase taxol production relationship. However, the inoculants of this invention do not require going through that growth phase before the production of taxane compounds commences. Rather, the inoculation or transformation of the cambium tissue by introduction of Agrobacterium not only does not interfere with the taxane compound production, but also it shifts the production into the growth phase, and at an increased concentration. As compared to the case of avirulent strains, the total yield in the case of gall tissue is higher because the total tissue biomass which produces the taxane compounds is greater due to more rapid growth. But the increased concentration of taxanes in the avirulent strain also yields greater production as compared to normal tissue.

While any of the ten species of the genus Taxus and hybrids may be employed, I prefer to work with *Taxus baccata* (English or Irish yew), *Taxus wallichiana, Taxus cuspidata, Taxus canadensis, Taxus chinensis, Taxus brevifolia*, and hybrids such as *Taxus X media* as the seedling, cutting, and tree management characteristics of these species are the most well known. The preferred species is *Taxus baccata* and its hybrids. In addition, any of the virulent or avirulent Agrobacterium strains may be used, with a virulent strain of *Agrobacterium tumefaciens* being preferred. Other living prokaryotic microbial vectors may be used, such as naturally occuring soil bacteria. e.g. Pseudomonas, Xanthomonas, Rhizobium, Agrobacterium and the like prokaryotes. They may be used alone or in combination with chemical or mechanial vectors. Other suitable vectors are those known to cause galls, such as insect or physical injury. One example of chemical or biologic agents is treatment of bark or other tissues with natural or synthetic growth regulators (such as NAA and/or kinetin), or other compounds which mimic the effect of infection with virulent or avirulent strains of Agrobacterium. While we do not wish to be bound by theory, the avirulent strains may function as taxane production elicitors.

Inoculation of the Taxus plants may be begun in the early seedling stage, and may be accomplished by any suitable mechanical process of introduction of the vector (Agrobacterium) into the cambium, e.g. by stabbing with a needle dipped in a culture of Agrobacterium, infusion via Agrobacterium-soaked patches, or use of a particle gun employing microscopic metallic, plastic or cellulose particles laden (coated or containing) Agrobacterium which are fired into the cambium via compressed gas. Considering the large number of galls which must be induced for the biomass production needed for substantial taxol/taxane production, use of a particle gun employing hollow, thin-shelled plastic, cellulose or starch microspheres containing the Agrobacterium appears an efficient method of inoculation. The microspheres may be produced from a solution of starch or cellulose containing the Agrobacterium which is formed into microspheres by a spray dryer. These are expected to have sufficient integrity and durability to be fired into the cambium through overlying tissue in young plants.

This invention also includes the in vivo use of genetically engineered strains of Agrobacterium which include gene coding to influence production of a selected secondary metabolite product. In addition, use of growth regulators may be combined with product precursors or effectors of products to increase the yield of the selected products.

DESCRIPTION OF THE BEST MODE

The following detailed description illustrates the invention by way of example, not by way of limitation of the principles of the invention. This description will clearly enable one skilled in the art to make and use the invention, and describes several embodiments, adaptations, variations, alternatives and uses of the invention, including what I presently believe is the best mode of carrying out the invention.

COMPARATIVE EXAMPLES

The examples below demonstrate that tissues of the genus Taxus are susceptible to infection and transformation by the bacterium *Agrobacterium tumefaciens*. Infection of bark tissue (cambium) with the virulent strain A281 results in gall formation at the site of the infection. In contrast, infection with the non-virulent strain LBA4011 or by physical wounding did not result in the vast cambial cell proliferation characteristic of gall formation, although a wound response was noted and the wound site tissue showed approximately twice the taxane concentration as compared to adjacent normal tissue.

INOCULATION AND GALL FORMATION

Four to 6 months old cuttings from a Taxus plant, taxonomically classified as *Taxus baccata*, was infected with both A281 (virulent) and LBA4011 (avirulent) strains of *Agrobacterium tumefaciens* grown on conventional liquid M9 medium. The infection was produced by stabbing mature and immature stem and leaf tissue with a hypodermic needle dipped into liquid suspensions of the two Agrobacterium strains. The stab sites were marked to properly identify the strains used at the respective sites.

Swelling of stem tissue at the site of the A281 infection was evident within 1-2 months after inoculation. The swelling, as determined by stem diameter measurements, indicated that the cambium was proliferating at the site of the infection at 2-3 times the rate of normal stem tissue above and below the site. Galls formed were deemed large enough for harvestinq after 9 months, and were removed simply by slicing from the stem with a scalpel, knife or razor blade. Galls did not form at LBA4011 (avirulent) sites.

TABLE 1

| Increased Biomass Due to Gall Formation | | | |
|---|---|---|---|
| | Stem Diameter in CM | | |
| | Above Gall | Gall | Below Gall |
| Site 1 (Lower Stem) | .9 | 1.6 | 1.0 |
| Site 2 (Upper Stem) | .7 | 1.1 | .8 |
| Site 3 (Upper Stem) | .7 | 1.3 | .8 |

Site 1 was a gall on the lower stem.
Sites 2 and 3 were two galls side by side, showing that a plant can support closely spaced galls.

TRANSFORMATION

To show transformation had occurred by the infection, Gall tissue which formed at the site of infection with strain A281 was first sprayed with 70% isopropyl alcohol. A sterile scalpel was used to excise a section of gall tissue which included both bark and living tissue. This tissue was immediately dropped into 10% commercial bleach containing 2 drops per 100 ml Tween 80 and shaken for 10 minutes. Tissue was rinsed for 10 minutes in sterile water. Sterile tissue was cut into approximately 0.5-1.0 mm slices and placed on B5 basal medium without growth regulators and containing 3% sucrose and 500 ug/ml cefotaxime and carbenicillin in the dark at 24° C. Subsequently, callus tissue formed from this sterilized tissue sample, and callus growth continued upon subsequent transfer. The callus continues to grow in the absence of plant growth regulators.

IN VIVO GALL TISSUE TAXOL/TAXANE PRODUCTION

Samples were removed from A281, LBA4011 and non-infected stem tissue, and analyzed for taxol (HPLC methods) and taxanes (ELISA method). Both bark tissues alone, and bark plus living tissues (deeper cut into stem), were harvested and analyzed. The results of the analysis of the harvested samples are presented in Table 2.

TABLE 2

| Comparative Taxane Content of Tissue; Infected (Virulent vs. Avirulent) vs Non-Infected | |
|---|---|
| Tissue Type | Taxanes. ug/gFW |
| Infected Virulent Gall (Woody) | 15.4 |
| Infected Virulent Gall (Woody & Living) | 28.4 |

TABLE 2-continued

Comparative Taxane Content of Tissue; Infected (Virulent vs. Avirulent) vs Non-Infected

| Tissue Type | Taxanes. ug/gFW |
|---|---|
| Infected Wound Avirulent (Woody & Living) | 25.4 |
| Non-Infected (Normal) (Woody & Living) | 14.4 |

"Woody" tissue is mostly outer bark;
"Woody & Living" is outer bark tissue plus underlying tissue into heartwood.

DISCUSSION

Both visual observations and measurements clearly show virulent Agrobacterium infection results in very substantially greater biomass production than normal, non-infected stem tissue. In addition, the continued growth (regrowth) of gall tissue from sites where gall tissue had been incompletely harvested (e.g. by a tangential slice without excising completely around and outside the gall area and radially into the stem "underneath" the gall) clearly indicates that this is a renewable resource.

Taxol production in the most rapidly growing tissue of Taxus plants, e.g. new leaves and meristems, are known to have the lowest concentration of taxol. Conversely, non-growing or very slowly growing tissues (e.g. mature leaves and bark) have the highest concentration of taxol, hence the post-growth "coupling" phenomenon.

The issue was whether the Agrobacterium transformation would do two things: First, change the secondary metabolites, and second, affect the post-growth phase production of taxol/taxane compounds. Unexpectedly and fortunately, there was an effect on post-growth phase production of taxol/taxane compounds. The assays showed that the post-growth association was uncoupled, i.e. taxol/taxane compound production was shifted into the gall and inoculant cambial growth proliferation stage. Further, the taxol/taxane production did not interfere with the rate of cell proliferation, and the cambial proliferation continued unabated. In addition, the secondary metabolites included taxol/taxane-type compounds, and were present in greater concentration per unit mass. Not only was there greater concentration, but also greater total mass. Finally, the callus tissue from the gall tissue growth was hormone autotrophic.

What was found was that the taxol concentration in gall tissue was twice that of adjacent non-infected stem tissue, 28.4 ug/gFW vs 14.4 ug/gFW (micrograms per gram of fresh weight). It is important to note that surprisingly, infection by the avirulent strain (LBA4011) also resulted in a doubling of the concentration of taxanes, an increase equal to that of the virulent area, as compared to the non-infected stem tissue. But the biomass of the avirulent area did not show a substantial increase.

It should be understood that various modifications within the scope of this invention can be made by one of ordinary skill in the art without departing from the spirit thereof. I therefore wish my invention to be defined by the scope of the appended claims in view of the specification as broadly as the prior art will permit.

I claim:

1. A method of in vivo production of taxanes comprising the steps of:
   a) inoculating a plant of the genus Taxus with *Agrobacterium tumefaciens* virulent strain A281 in at least one site on said plant;
   b) sustaining said plant for a time sufficient to induce said plant to respond with in vivo growth of gall tissue exhibiting production of secondary metabolites at the site of said inoculation;
   c) harvesting at least some of said gall tissue from said site; and
   d) extracting a taxane from said harvested gall tissue.

2. A method of in vivo taxane production as in claim 1 wherein:
   a) said induced gall tissue is incompletely harvested; and
   b) continuing to sustain said plant for a time sufficient to induce said plant inoculation site to produce gall regrowth which may be harvested as a renewable resource.

3. A method of in vivo taxane production as in claim 2 wherein:
   a) said plant is selected from the group consisting essentially of the species *Taxus baccata, Taxus wallichiana, Taxus chinensis, Taxus cuspidata, Taxus canadensis, Taxus brevifolia* and hybrids thereof.

4. A method of in vivo taxane production as in claim 3 wherein:
   a) said plant is a *Taxus baccata* or hybrid thereof.

5. A method of in vivo taxane production as in claim 1 wherein:
   a) said extraction step includes solvent extraction of taxanes.

6. A method of in vivo taxane production as in claim 5 wherein:
   a) said solvent extraction solvent is selected from the group consisting essentially of ether, methanol, ethanol, methylene chloride, and mixtures thereof.

7. A method of in vivo production of taxanes comprising the steps of:
   a) inoculating a plant of the genus Taxus with *Agrobacterium tumefaciens* avirulent strain LBA4011 in at least one site on said plant;
   b) sustaining said plant for a time sufficient to induce said plant respond with growth of wound response tissue at the site of said inoculation, said wound response tissue exhibiting production of at least one taxane compound in excess of the production of surrounding normal, healthy plant tissue;
   c) harvesting at least some of said wound response tissue from said site; and
   d) extracting a taxane from said harvested wound response tissue.

8. A method of in vivo taxane production as in claim 7 wherein:
   a) said induced wound response tissue is incompletely harvested; and
   b) continuing to sustain said plant for a time sufficient to induce said plant inoculation site to produce wound response regrowth which may be harvested as a renewable resource.

9. A method of in vivo taxane production as in claim 8 wherein:
   a) said plant is selected from the group consisting essentially of the species *Taxus baccata, Taxus wallichiana, Taxus chinensis, Taxus cuspidata, Taxus canadensis, Taxus brevifolia* and hybrids thereof.

10. A method of in vivo taxane production as in claim 9 wherein:
    a) said plant is a *Taxus baccata* or hybrid thereof.

11. A method of in vivo taxane production as in claim 7 wherein:
    a) said extraction step includes solvent extraction of taxanes.

12. A method of in vivo taxane production as in claim 11 wherein:
    a) said solvent extraction solvent is selected from the group consisting essentially of ether, methanol, ethanol, methylene chloride, and mixtures thereof.

* * * * *